(12) United States Patent
Linares

(10) Patent No.: US 8,758,439 B2
(45) Date of Patent: *Jun. 24, 2014

(54) SPINE SUPPORT IMPLANT INCLUDING INTER VERTEBRAL INSERTABLE FLUID BALLASTABLE INSERT AND INTER-VERTEBRAL WEB RETAINING HARNESSES

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 88 days.

This patent is subject to a terminal disclaimer.

(21) Appl. No.: 13/397,853

(22) Filed: Feb. 16, 2012

(65) Prior Publication Data

US 2012/0150303 A1 Jun. 14, 2012

Related U.S. Application Data

(63) Continuation-in-part of application No. 12/273,067, filed on Nov. 18, 2008.

(60) Provisional application No. 60/988,921, filed on Nov. 19, 2007.

(51) Int. Cl.
*A61F 2/44* (2006.01)

(52) U.S. Cl.
USPC ...................................... 623/17.11

(58) Field of Classification Search
USPC ............ 606/246, 250–278; 623/17.11–17.16
See application file for complete search history.

(56) References Cited

U.S. PATENT DOCUMENTS

| | | |
|---|---|---|
| 5,522,899 A | 6/1996 | Michelson |
| 5,653,763 A | 8/1997 | Errico et al. |
| 5,683,391 A | 11/1997 | Boyd |
| 5,782,832 A | 7/1998 | Larsen et al. |
| 6,001,130 A | 12/1999 | Bryan et al. |
| 6,045,579 A | 4/2000 | Hochshuler et al. |
| 6,228,085 B1 | 5/2001 | Theken et al. |
| 6,447,546 B1 | 9/2002 | Bramlet et al. |
| 6,626,904 B1 | 9/2003 | Jammet et al. |
| 6,626,909 B2 | 9/2003 | Chin |
| 6,641,614 B1 | 11/2003 | Wagner et al. |
| 6,645,207 B2 | 11/2003 | Dixon et al. |
| 6,736,850 B2 | 5/2004 | Davis |
| 6,936,071 B1 | 8/2005 | Marnay et al. |
| 7,201,775 B2 | 4/2007 | Gorensek et al. |
| 7,276,082 B2 | 10/2007 | Zdeblick et al. |

(Continued)

FOREIGN PATENT DOCUMENTS

WO   WO-2008011492 A2   1/2008

*Primary Examiner* — Mary Hoffman
*Assistant Examiner* — Michelle C Eckman
(74) *Attorney, Agent, or Firm* — Gifford, Krass, Sprinkle, Anderson & Citkowski, P.C.; Douglas J. McEvoy

(57) ABSTRACT

An implant support device associated with succeeding spinal vertebrae, including a harness exhibiting a plurality of legs, each extending from a rotatable bearing or suitable interconnecting support. Each of the legs terminates in an angled tang, this being engaged with a surface of a selected vertebrae. Additional features include undercut portions defined between the legs and arcuate/hemispherical mounting locations surrounding the bearing in individually rotatably permitting fashion. Inter-vertebral support cushions are also positioned between succeeding vertebrae, and can be incorporated with or provided separately from the web support harnesses.

7 Claims, 7 Drawing Sheets

(56) References Cited

U.S. PATENT DOCUMENTS

| | | | |
|---|---|---|---|
| 7,316,714 B2 | 1/2008 | Gordon et al. | |
| 7,320,707 B2 | 1/2008 | Zucherman et al. | |
| 7,344,564 B2 | 3/2008 | Sweeney | |
| 7,473,269 B1 | 1/2009 | Hynes | |
| 7,507,243 B2 | 3/2009 | Lambrecht et al. | |
| 7,563,283 B2 | 7/2009 | Kwak | |
| 7,575,577 B2 | 8/2009 | Boyd et al. | |
| 7,585,316 B2 | 9/2009 | Trieu | |
| 7,585,325 B2 | 9/2009 | Schneid et al. | |
| 7,604,654 B2 | 10/2009 | Fallin et al. | |
| 7,655,045 B2 | 2/2010 | Richelsoph | |
| 7,682,376 B2 | 3/2010 | Trieu | |
| 7,763,052 B2 | 7/2010 | Jahng | |
| 7,766,966 B2 | 8/2010 | Richelsoph | |
| 7,776,069 B2 | 8/2010 | Taylor | |
| 7,901,434 B2 | 3/2011 | Drewry et al. | |
| 7,909,852 B2 | 3/2011 | Boomer et al. | |
| 2002/0022887 A1 | 2/2002 | Huene | |
| 2002/0143329 A1 | 10/2002 | Serhan et al. | |
| 2004/0015166 A1 | 1/2004 | Gorek | |
| 2004/0030398 A1 | 2/2004 | Ferree | |
| 2004/0082998 A1 | 4/2004 | Shinomiya et al. | |
| 2004/0210226 A1* | 10/2004 | Trieu | 606/72 |
| 2005/0113927 A1 | 5/2005 | Malek | |
| 2005/0131406 A1* | 6/2005 | Reiley et al. | 606/61 |
| 2005/0216004 A1 | 9/2005 | Schwab | |
| 2005/0216087 A1 | 9/2005 | Zucherman et al. | |
| 2005/0245930 A1 | 11/2005 | Timm et al. | |
| 2005/0256578 A1* | 11/2005 | Blatt et al. | 623/17.15 |
| 2005/0277930 A1 | 12/2005 | Parsons | |
| 2006/0009851 A1 | 1/2006 | Collins et al. | |
| 2006/0036240 A1 | 2/2006 | Colleran et al. | |
| 2006/0084984 A1 | 4/2006 | Kim | |
| 2006/0085074 A1 | 4/2006 | Raiszadeh | |
| 2006/0149230 A1 | 7/2006 | Kwak et al. | |
| 2006/0229609 A1* | 10/2006 | Wang | 606/61 |
| 2006/0235414 A1* | 10/2006 | Lim et al. | 606/73 |
| 2006/0241601 A1* | 10/2006 | Trautwein et al. | 606/61 |
| 2006/0241766 A1 | 10/2006 | Felton et al. | |
| 2006/0276898 A1 | 12/2006 | Jackson | |
| 2006/0282078 A1 | 12/2006 | Labrom et al. | |
| 2007/0005062 A1 | 1/2007 | Lange et al. | |
| 2007/0083199 A1 | 4/2007 | Baccelli | |
| 2007/0093829 A1 | 4/2007 | Abdou | |
| 2007/0112428 A1 | 5/2007 | Lancial | |
| 2007/0168036 A1 | 7/2007 | Ainsworth et al. | |
| 2007/0168039 A1 | 7/2007 | Trieu | |
| 2007/0185489 A1 | 8/2007 | Abdou | |
| 2007/0213719 A1* | 9/2007 | Hudgins et al. | 606/61 |
| 2007/0225813 A1 | 9/2007 | Haines | |
| 2007/0233089 A1* | 10/2007 | DiPoto et al. | 606/61 |
| 2007/0288011 A1* | 12/2007 | Logan | 606/61 |
| 2008/0021466 A1 | 1/2008 | Shadduck et al. | |
| 2008/0039943 A1 | 2/2008 | Le Couedic | |
| 2008/0114358 A1* | 5/2008 | Anderson et al. | 606/64 |
| 2008/0183294 A1* | 7/2008 | Adl | 623/17.16 |
| 2008/0269904 A1* | 10/2008 | Voorhies | 623/17.16 |
| 2009/0112266 A1* | 4/2009 | Weng et al. | 606/257 |
| 2010/0222820 A1 | 9/2010 | Trieu | |
| 2011/0029084 A1 | 2/2011 | Milbocker et al. | |
| 2011/0224793 A1 | 9/2011 | Fortin et al. | |

* cited by examiner

SPINE SUPPORT IMPLANT INCLUDING INTER VERTEBRAL INSERTABLE FLUID BALLASTABLE INSERT AND INTER-VERTEBRAL WEB RETAINING HARNESSES

CROSS-REFERENCE TO RELATED APPLICATIONS

This Application is a Continuation-in-part of application Ser No. 12/273,067 filed on Nov. 18, 2008, which in turn claims the benefit of U.S. Provisional Application 60/988,921 filed on Nov. 19, 2007.

FIELD OF THE INVENTION

The present invention teaches a improved applications of spinal support implants, these relating in particular to versions of web harness supports for use with succeeding vertebrae and which, in combination with selective cushioning implants or integrally defined and displaceably mounted disk portions formed with the web harnesses, operate to provide a degree of movement permitting support to a damaged spinal column, short of requiring the vertebrae be fused together. By virtue of avoiding the prior art necessity of fusing selected vertebrae within the spinal column, the remaining (non-fused) vertebrae are prevented from being overloaded, which will otherwise occur, and suffering premature damage.

BACKGROUND OF THE INVENTION

The prior art is well documented with varying examples of inter-vertebral positioning and supporting devices. The advantage in each instance is to fuse or immobilize the vertebrae, such as in response to injury or illness. Fusing or immobilizing inter-vertebral movement is often necessary in order to prevent ongoing discomfort or pain which can result from undesirable contact between misaligned or misshapen vertebrae, in particular when the spinal nerve column or its individual branches are affected.

Examples of known inter-vertebral stabilization devices are such as those set forth in US 2007/0093829 to Abdou and U.S. Pat. No. 6,645,207 to Dixon. Other insert or repair structures are also known, and which are positioned between opposing annular (or body) portions of succeeding vertebrae. One example of this is set forth in the disk repair structure Zucherman 2005/0216087. Additional examples include the artificial spinal fusion implants in Michelson, U.S. Pat. No. 5,522,899, as well as in U.S. Pat. No. 5,782,832, to Larsen. Additional examples include the spine stabilization systems of Gorek 2004/0015166 and Malek 2005/0113927 and the posterior stabilization system of Kwak 2006/0149230.

SUMMARY OF THE INVENTION

The present invention discloses a spinal support implant for positionally securing succeeding vertebrae associated with a spinal column. Each of the preferred variants includes one or more web retaining harnesses, each of which exhibits a plurality of hardened plastic legs extending from central and hemi-spherical mounting locations. These hemispherical location include such as overlapping portions surrounding a central bearing in secured and rotatively permissive fashion.

The legs each include, at remotely extending ends, such as tangs/detents that securely mount to such as undercut locations in the individual vertebrae. In this fashion, the web harness generally and positionally immobilizes the successive spinal vertebrae to which it is attached, and while permitting a minor degree of misalignment and movement, such as is common in normal spinal activity, this again being prevented by such conventional alternate procedures as spinal fusion utilizing anchoring screws and plates.

An inter-vertebral support cushion can be provided separately or in integral combination with the web-retaining harness and which defines and additional component of the present invention which can be pre-positioned between succeeding vertebrae. In one variant, and following being pre-positioned in location (such as between opposing body or annular facing surfaces of succeeding disks) the bladder configured cushion can be selectively injection pressurized with a fluid, this in order to establish a given bias pressure. Another version of the present inventions combines the web support harnesses and inter-vertebral support cushions into a single article, which again features the hardened plastic legs extending from central and hemi-spherical mounting locations integrally formed with an edge location of the disk portion surrounding a central bearing in secured and rotatively permissive fashion, the legs again including tangs/detents that securely mount to such as undercut locations in the individual vertebrae.

An additional variant depicts a spherical support extending from a side edge location of an inter-vertebral inserted disk or cushioning member. A plurality of individual and elongated members, such as depicted in upper and lower pairs, are provided, each of which including a mini-spherical shaped lower end which is seated within a mating and substantially spherical shaped communicating socket interior defined in the spherical support.

Opposite remote extending ends of the elongated members are anchored in any suitable fashion to surface locations of the vertebrae In this fashion, the vertebrae are permitted a degree of limited movement by virtue of the range of eccentric pivoting motion of the elongate members about their mini-spherical ends seated within the spherical support defined sockets.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

Figure 1:
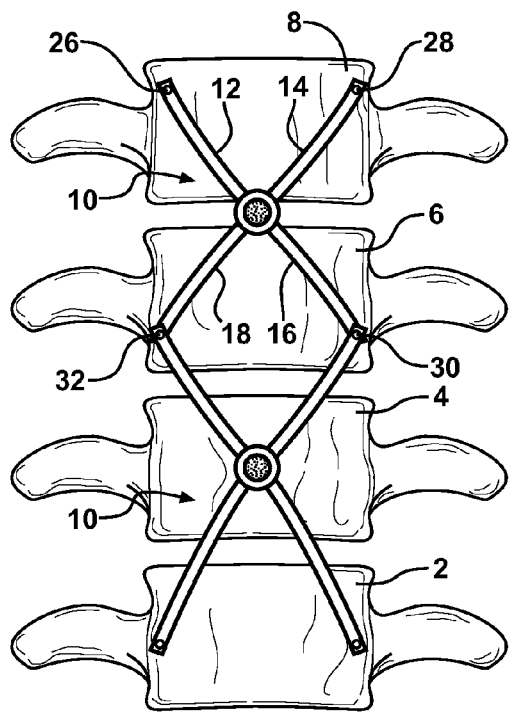
FIG. 1 is a plan view illustration of one arrangement of a web retaining harness associated with a plurality of vertebrae forming a part of a spinal column according to an embodiment of the present inventions and for controllably and displacingly supporting successive vertebrae.

FIG. 1 is an illustration of a first arrangement of a web retaining harness 10 for controllably and displacingly supporting successive vertebrae, and as are shown at 2, 4, 6 and 8, forming a part of a spinal column. As previously discussed, the several variants of vertebral support implants, as disclosed herein, operate to provide a degree of movement permitting support to a damaged spinal column, and short of requiring the vertebrae be fused together as is conventionally performed in an attempt to address many spinal injuries, but which typically result in the patient experiencing significant losses in spinal mobility.

Figure 3:
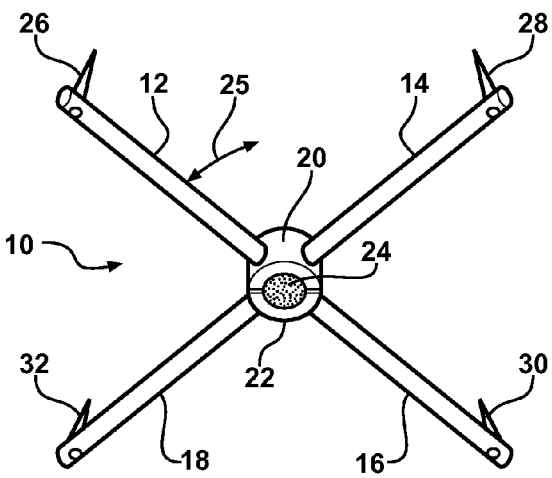
FIG. 3 is an illustration of a selected support harness and illustrating features such as hardened plastic legs extending from central and hemi-spherical mounting locations surrounding a central bearing in secured and rotatively permissive fashion, and including tangs/detents that securely mount to such as undercut locations in the individual vertebrae.
Figure 3A:
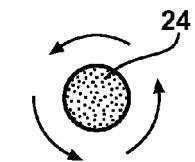
FIG. 3A is a partial view of a selected and inner most located bearing.
Figure 3C:
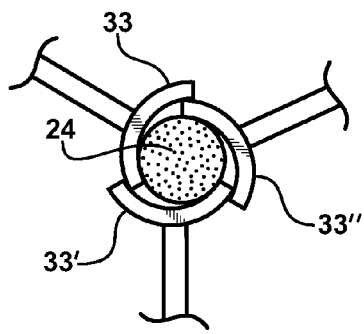
FIG. 3C is a yet further partial view and illustrating a multiple overlapping relationship established by a plurality of three leg supporting annulus and bearing surface contact portions.

As is also described in reference to FIGS. 3-3C, the web support harness is illustrated as a pair of identically configured harnesses 10, typically each including hardened plastic legs, see at 12, 14, 16 and 18. The legs each extend from central and hemi-spherical mounting locations, see at 20 and 22 in FIG. 3, these in turn surrounding a central bearing 24 in secured and rotatively permissive fashion.

While not limited to any specific material composition, the legs 12-18 can exhibit a composite plastic with sanitary or antibiotic properties and can further establish a desired degree of flex (or bend) so as to provide considerable positional engagement of the associated vertebrae, and while still providing for any incrementally (or minor) desired degree of movement between the vertebrae. In this fashion, the vertebrae are positionally immobilized to the degree desired, while at the same time the patient may still be provided with some minor degree of residual movement or flexibility, this consistent with the material aspects of the harness leg construction.

As shown in FIG. 3, one or more of the pairs of legs (e.g. see as again shown at 12 & 14, as well as at 16 & 18) can extend from each of first 20 and second 22 hemi-spherical (or arcuate) mounting locations, it being understood that the overlapping mounting locations are further capable of being constructed according to other shapes and configurations, and such that the legs 12-18 can exhibit respective degrees of flexibility, both individually and vis-à-vis one another. In this fashion, any degree of permissible rotation of the arcuate portions (e.g. hemi-spherical) 20 and 22 are transferred to the individual and integrally extending pairs 12 & 14 and 16 & 18 of legs. Each of the legs 12-18 further includes tangs (or prong shaped detents), see as respectively shown at 26, 28, 30 and 32 in FIG. 3, these being integrally formed at the outboard ends of the associated legs and which securely mount to such as drilled undercut locations formed in each of the individual vertebrae 2, 4, 6, and 8.

Figure 7:
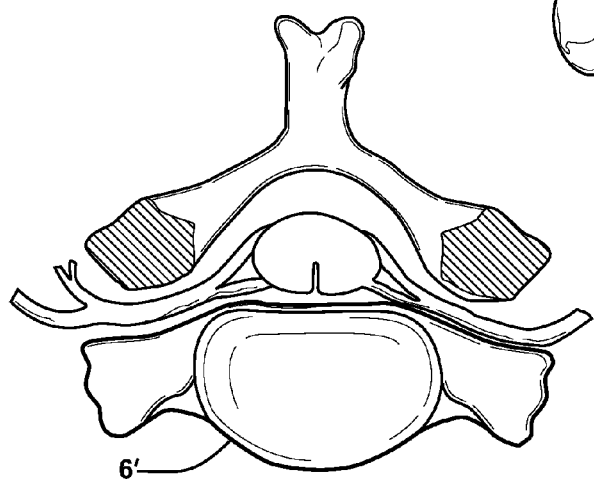
FIG. 7 is a top view of a vertebrae such as is also shown in FIG. 6 and such as is known in the Prior Art.

Although not illustrated, it is also envisioned that alternate fasteners can be employed for mounting the extending ends of the web harness legs to the associated vertebrae at locations which will promote optimal inter-vertebral stability and while allowing the vertebrae the possibility of exhibiting minor incremental degrees of flex or bend. In this fashion, any significant misalignment between vertebrae is prevented, and such as which could otherwise entail the undesirable incidence of pinching of the spinal nerve column (see as shown in the Prior Art illustration of FIG. 7 as associated with selected spinal vertebrae 6').

As further again shown at 24 in FIG. 3A, a partial view of a selected and inner most located bearing (see also FIGS. 1 and 3) is illustrated and which can include such as heavy duty nylon or other suitable material construction. As previously described, the first 20 and second 22 hemi-spherical (or arcuate) mounting locations are formed in mutually contacting and edge overlapping fashion, these encasing the centrally positioned bearing 24 and so that the bearing facilitates a desired degree of "give" or rotational support (see arrow 25 in FIG. 3 in relation to selected leg 12). It is also envisioned that the legs illustrated herein can be attached to such as undercut portions associated with the bearing mounting locations and in order to provide an alternate mounting variant.

Figure 3B:
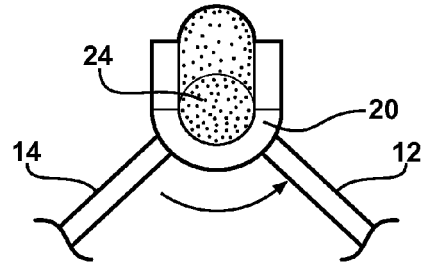
FIG. 3B is a further partial view illustrating a selected bearing and partial overlapping annulus contact associated with a given engagement leg.

FIG. 3B is a further partial view (with selected contact portion 22 removed) and illustrating bearing 24 and overlapping contact portion 20, from which extend each of the plurality of legs 12-18. It is also understood that the individual and arcuate shaped contact portions (e.g. again at 20 and 22) can exhibit any relative shape, as well as configuration for interconnecting in relative rotatable freedom about the bearing 24, the purpose for which being to impart a desired degree of rotational give or bend to the individual legs.

FIG. 3C is a yet further partial view and illustrating multiple and mutually overlapping edges established by a plurality of three leg supporting annulus and bearing surface contact portions, see at 33, 33' and 33", these surrounding the central bearing 24 As shown in FIG. 3c, individual extending legs (illustrated in reduced length) extend from the individual overlapping and bearing surface contact portions, it being understood that any plurality of legs as well as any number of individual bearing surface supported and overlapping contact portions, can be provided and which establish any desired degree of inter-rotation, bend or give to the individual legs.

Figure 2A:
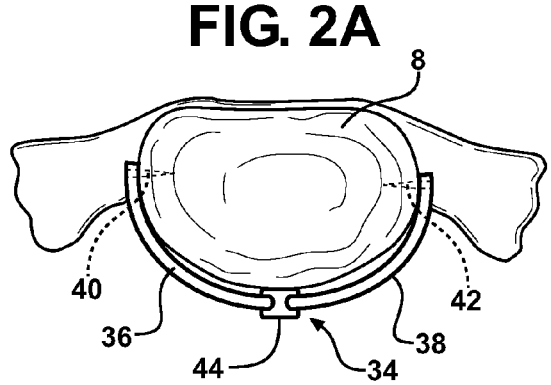
FIG. 2A is a top view of a further configuration of web support harness according to the present inventions.

Referring now to FIG. 2A, a top view of a further configuration of web support harness, see at 34, and specifically illustrating the feature of the associated legs 36 and 38 angled in order that the end defined tangs, at 40 and 42, are mounted to substantially peripheral (outer) most defined locations associated with the selected vertebrae 8. The illustration of FIG. 2A further evidences the degree of flexibility (or bend) which is afforded the individual legs and in order to conformingly apply about the exterior periphery of the associated vertebrae. Referencing FIG. 2B, the peripheral location of the upper most extending pair of legs 36 & 38 and associated mounting detents 40 & 42 is again shown associated with the harness 34 and in contrast to the mounting arrangement of FIG. 1.

Figure 2B:
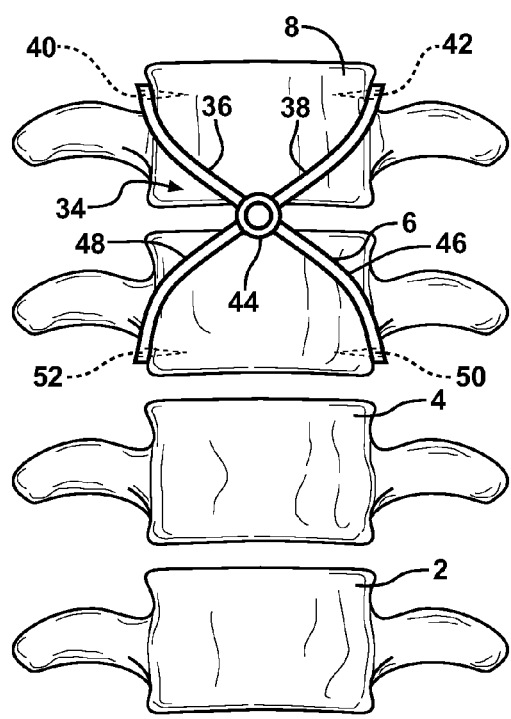
FIG. 2B is a plan view similar to FIG. 1 of the harness configuration shown in FIG. 2A, and illustrating peripheral engagement location of the of the mounting detents associated with the harness.

Consistent with that previously shown and described in reference to FIGS. 3-3C, the construction of each harness again includes a central bearing, about which is supported one or more rotatably permissive contact locations, e.g. at 44. As further shown in FIG. 2B, the harness 34 includes a second (lower) pair of legs 46 and 48 with associated detents 50 and 52 and which likewise engage peripheral most defined locations associated with the succeeding vertebrae 6. The illustrations of FIGS. 1 and 2B are intended to demonstrate the range of possible mounting variations which are possible with the web support harness, and in particular the ability of the various extending legs to engage any suitable vertebral location, not limited to a peripheral edge or specified height location.

Figure 4:
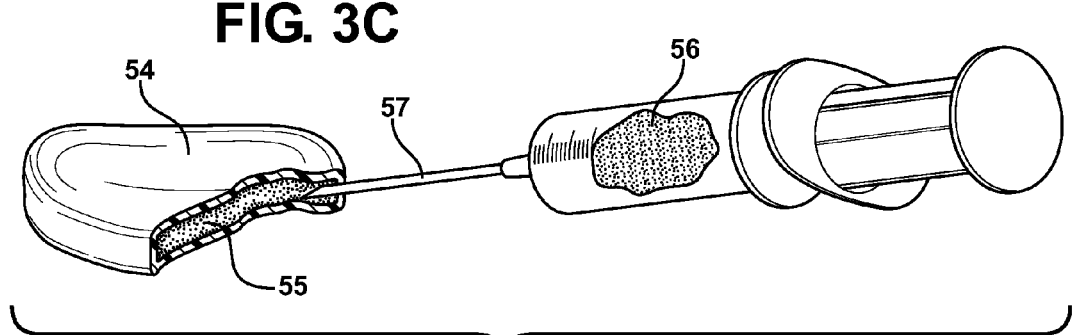
FIG. 4 is an illustration of an inter-vertebral support cushions defining a component of the present inventions and which is selectively injection pressurized with a suitable fluid medium in the manner illustrated.

Referencing now FIG. 4, an illustration is shown at 54 of an inter-vertebral support cushion, this defining a component which is capable of being used in combination with the web support harnesses 10. As shown, the cushion 54 is constructed of a flexible and fluid retaining (as well as sanitary) plastic exhibiting an open interior (see as shown at 55 in cutaway). A syringe 56 is provided and includes a projecting needle 57 which allows for a volume of fluid contained within the syringe cylinder to be injected into the support cushion 54.

Figure 5:
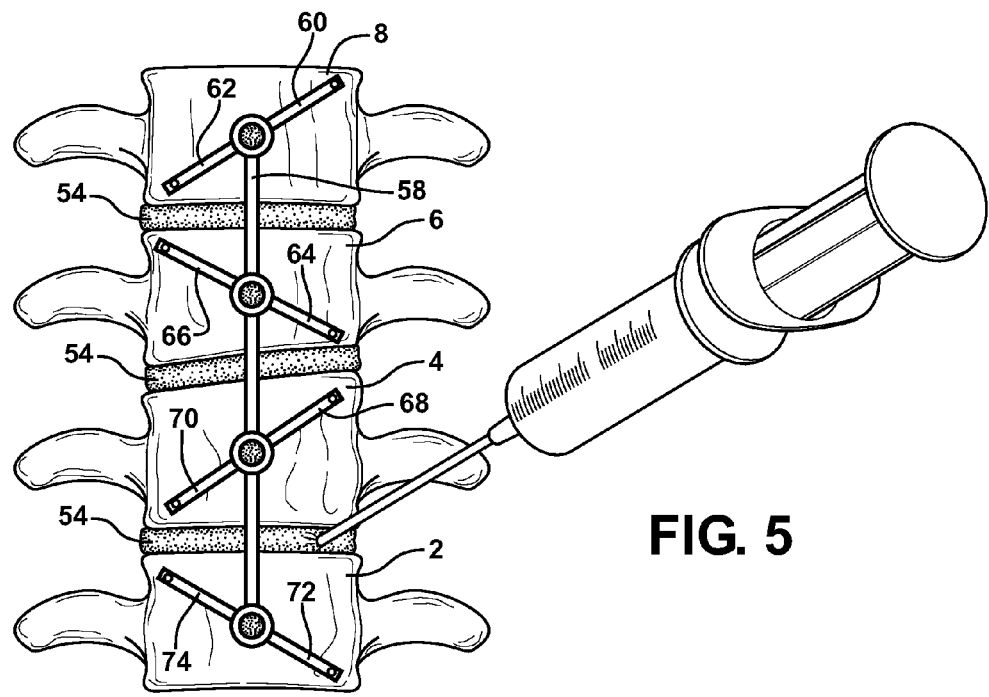
FIG. 5 is an illustration similar to FIG. 1, and showing a further example of combination inter-vertebral web support harnesses and cushions.

The construction and consistency of the cushion (or bag) 54 is such that it is capable of being pre-positioned between succeeding vertebrae, as shown in FIG. 5, following which it is selectively injection pressurized in the manner illustrated. FIG. 5 additionally illustrates an example of a combination of inter-vertebral web support harnesses and cushions 54. The web support harness illustrated in FIG. 5 differs from that previously described, and includes in the illustrated embodiment a lengthwise extending support, this shown by stem 58 extending in overlapping fashion over any number of successively positioned vertebrae, and from which extend pairs of legs 60 & 62, 64 & 66, 68 & 70, and 72 & 74. Each of the individual pairs of legs extending in angular offset from the lengthwise (inter-vertebral) extending support 58.

The individual pairs of legs in FIG. 5 further extend in diagonally and alternating offsetting fashion, and such that respective end defined tangs/detents associated with each pair of legs secure to upper and lower opposite end locations of a selected vertebrae 2-8, thereby position ally supporting the individual vertebrae via the lengthwise extending and central supporting stem 58. It is also envisioned that adhesives can be employed for securing the lengthwise and diagonally offsetting legs. Additionally, the fluid injectable cushions 54, upon being filled, are designed in one variant to cure and set, this to establish minimal/incremental degrees of permitted movement relative to opposing annulus surfaces of the central body portions of the individual vertebrae (see again FIG. 5), and the cushions are further prevented from dislodging from between the vertebrae by virtue of the exterior surface mounted web harnesses, and which may be provided along each of opposite exterior sides of a pair of interconnected vertebrae.

Figure 6:
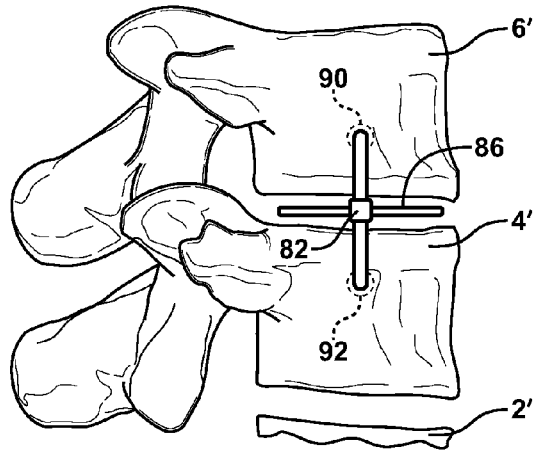
FIG. 6 is a side plan view of a further configuration of support column with combination support disc retaining web harness according to another embodiment of the present inventions.
Figure 8:
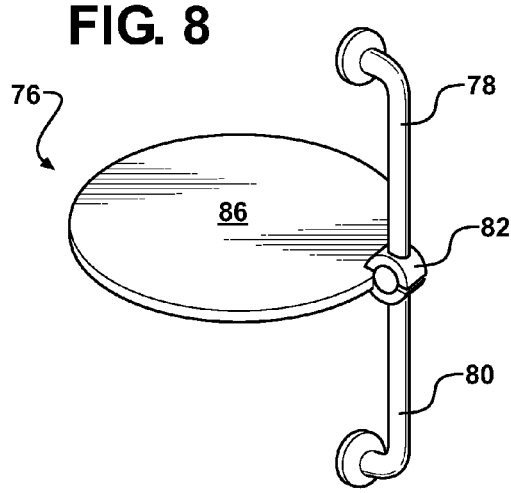
FIG. 8 is a perspective view of the combination disk and retaining web support harness according to the further preferred embodiment of FIG. 7.

Referring now to FIGS. 6 and 8, both perspective and side environmental plan views are shown of a further configuration of support column with combination support disc and retaining web harness 76, according to another embodiment of the present inventions. In particular, and is most clearly illustrated in each of FIG. 8 and the assembly views of FIGS. 9 and 9A, the combination disk and retaining web support harness includes the features of hardened plastic legs, see as shown at 78 and 80, these extending from central and hemispherical shaped mounting portions, at 82 and 84.

As further shown, an inter-vertebral disk inserting portion 86, such as also exhibiting a hardened surface, is integrally formed in extending fashion with an edge location of a selected mounting portion (in this instance 82). As shown in each of the side (FIG. 6) and ninety degree rotated (FIG. 9) views, the disk inserting portion 86 is positioned in the space established between a pair of opposing and succeeding annular body surfaces of selected vertebrae, subsequent to which the legs 78 and 80 are secured to surface locations of the succeeding vertebrae.

Figure 9:
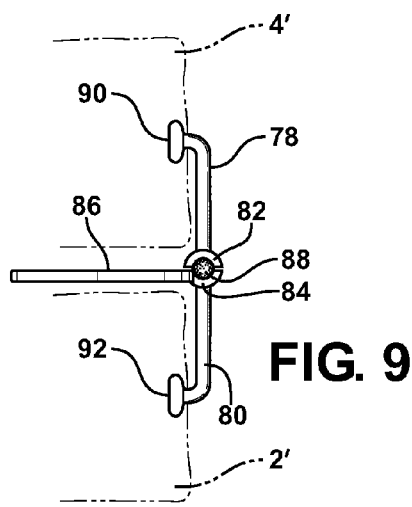
FIG. 9 is a side plan view of the combination disk and harness of FIG. 8 and further showing the features of the hardened plastic legs extending from central and hemi-spherical mounting locations integrally formed with an edge location of the disk portion and surrounding a central bearing in secured and rotatively permissive fashion, the legs again including tangs/detents that securely mount to such as undercut locations in the individual vertebrae.
Figure 9A:
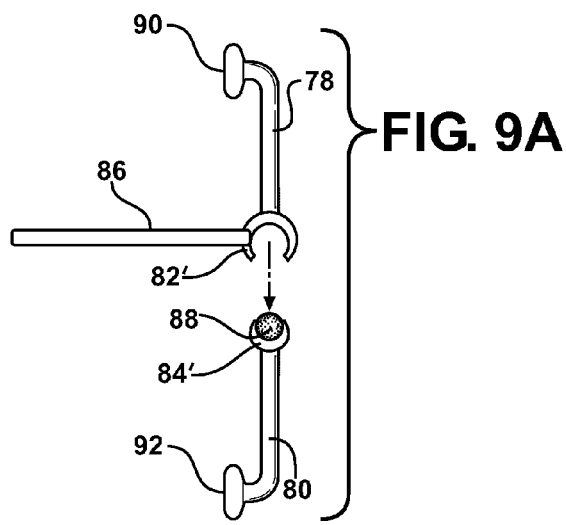
FIG. 9A is an exploded view of one configuration of leg and rotatable bearing as also shown in FIG. 9.

The variation of FIG. 9A differs somewhat from that shown in FIGS. 8 and 9, and by which the mounting portions are modified, see as shown at 82' and 84', such that the first portion 82' exhibits an enlarged inner arcuate recess, into which is resistively and snap-fit engaged the second (smaller dimensioned) portion 84'. The bearing is again shown at 88 and is sized so that it is supported upon the inner recess of the second mounting portion 84' and, upon snap fitting the first larger mounting portion 82' over the bearing 88 and second smaller portion 84', establishes a desired degree of movement between the legs 78 and 80.

The extending legs 78 and 80 each exhibit end-configured detents 90 and 92 which secure to such as again undercut locations (not shown) formed along the sides of the vertebrae. Accordingly, a modified range of motion is permitted between the legs 78 and 80, by virtue of the snap-fit arrangement established by the hemi-spherical portions 82 and 84 (or at 82' and 84' in FIG. 9A) about the spherical shaped bearing 88 supported therebetween. It is further understood that the combination disc support and retaining harness 76 can also be provided, either additionally or alternatively, to any of the harness or interior support cushion arrangements described herein.

Figure 10:
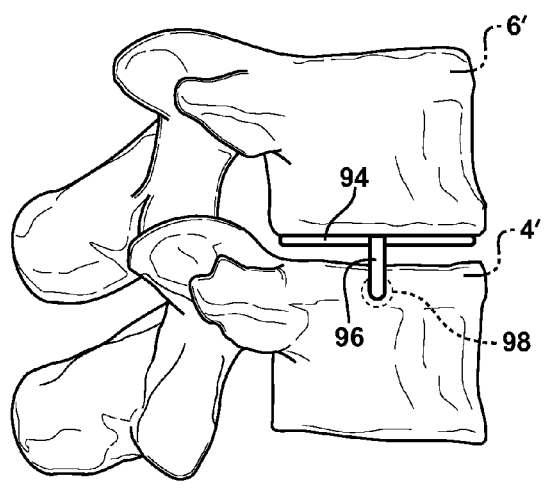
FIG. 10 is an illustration of an alternate mounting configuration of an inter-vertebral support disk.
Figure 10A:
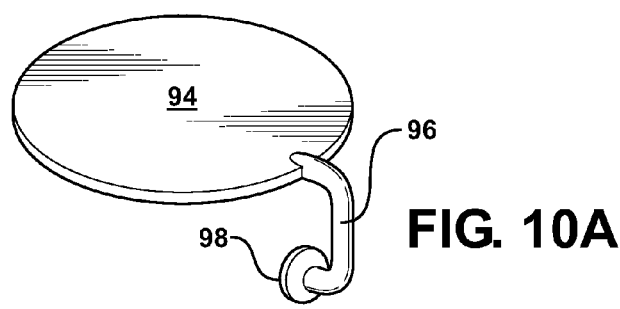
FIG. 10A is a further perspective illustration of the variant shown in FIG. 10.

FIGS. 10 and 10A illustrate a yet further alternate mounting configuration in which is provided an inter-vertebral support disk, see at 94. As opposed to the pair of support legs in the variant of FIG. 8, a single mounting location is provided by extending and inwardly angled leg 96 (this being illustrated substantially "L" shaped relative to the insertable disk portion 94) and which terminates in a single tang/detent mounting location 98. The purpose of the support disk 94 variant is, in part, to illustrate one of a number of potentially different configurations which can be employed in installing a combination central disc support and exterior surface engaging harness between succeeding spinal vertebrae.

Figure 11:
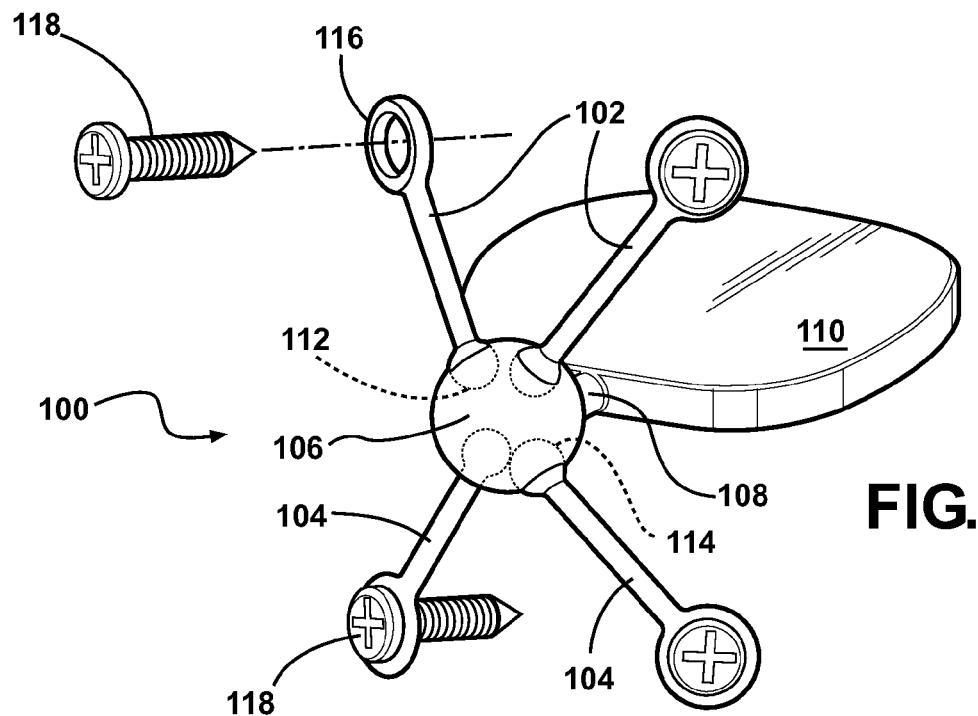
FIG. 11 is a perspective view of a further variant of retaining harness with eccentrically pivotally supported elongated members extending in upper and lower individually paired fashion from a spherical support extending from a side edge location of an inter-vertebral inserted disk or cushioning member.
Figure 12:
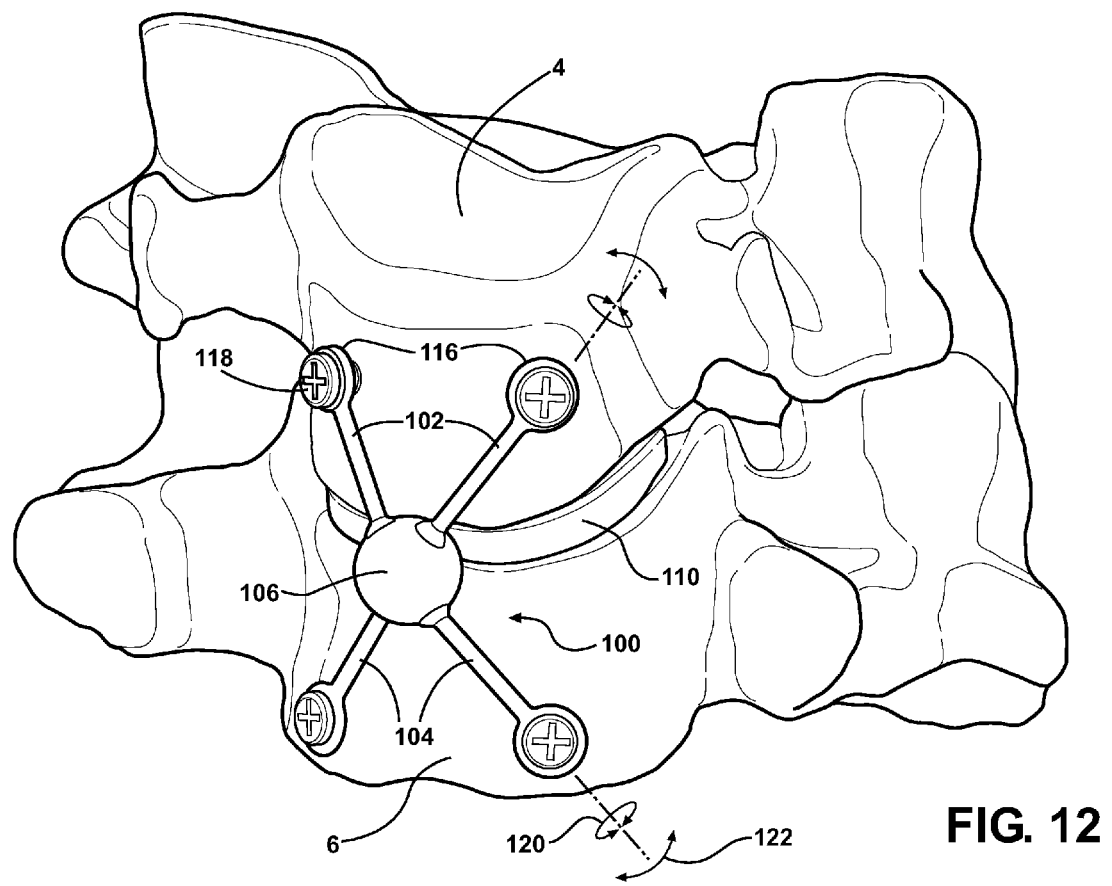
FIG. 12 is an environmental depiction of the retaining harness of FIG. 11 installed between succeeding vertebrae.

Referring now to FIG. 11, a perspective view is generally shown at 100 of a further variant of retaining harness with eccentrically pivotally supported elongated members, such as depicted in paired upper 102 and lower 104 extending fashion from a spherical support 106. The spherical support 106 extends, via a connecting projection or finger 108, from an exposed side edge location of an inter-vertebral inserted disk 110 or other suitable supporting and/or cushioning member, following implantation of the disk as depicted in FIG. 12. For purposes of description, the disk 110 can also be reconfigured as any of the previously described cushioning 54 in FIG. 4 or the hardened disks as exemplified at 86 in FIG. 8.

FIG. 12 is an environmental depiction of the retaining harness 100 of FIG. 11 installed between succeeding vertebrae. Of note, the upper 102 and lower 104 pairs of individual and elongated members (such as also termed as extending arms or leg) are each provided at first or inner pivotally connecting ends with a mini-spherical shaped portions (see in phantom at 112 and 114 in FIG. 11), these being seated within mating and substantially spherical shaped communicating socket interior locations defined at three dimensional surface offset locations in the spherical support 106 in both an eccentric and bearing-like supported fashion as will be further described.

Opposite remote extending ends of the elongated members 102 and 104 are configured with integrally defined eyelet locations, see for example best shown at 116 associated with selected upper extending elongated member 102 in FIG. 11, such that bone screws 118 are inserted through the open interior of each end configured eyelet 116 with the heads of the screws abutting against the sides of the eyelets in order to retain the harness upon anchoring of the screws within the indicated vertebrae mounting locations in FIG. 12. In this fashion, and upon mounting the harness 100 in the manner shown in FIG. 12, the vertebrae 4 and 6 are permitted a degree of inter-movement by virtue of eccentric (both rotational and pivotal) motion of the elongate members about their mini-spherical ends seated within the spherical support defined sockets, see both rotational 120 and pivotal 122 directional arrows. The effect of this mounting arrangement is that the elongated members each establish a desired three dimensional bearing relationship with the spherical support 106, this providing the desired and limited degree of inter-movement between the succeeding vertebrae 4 and 6.

Figure 13:
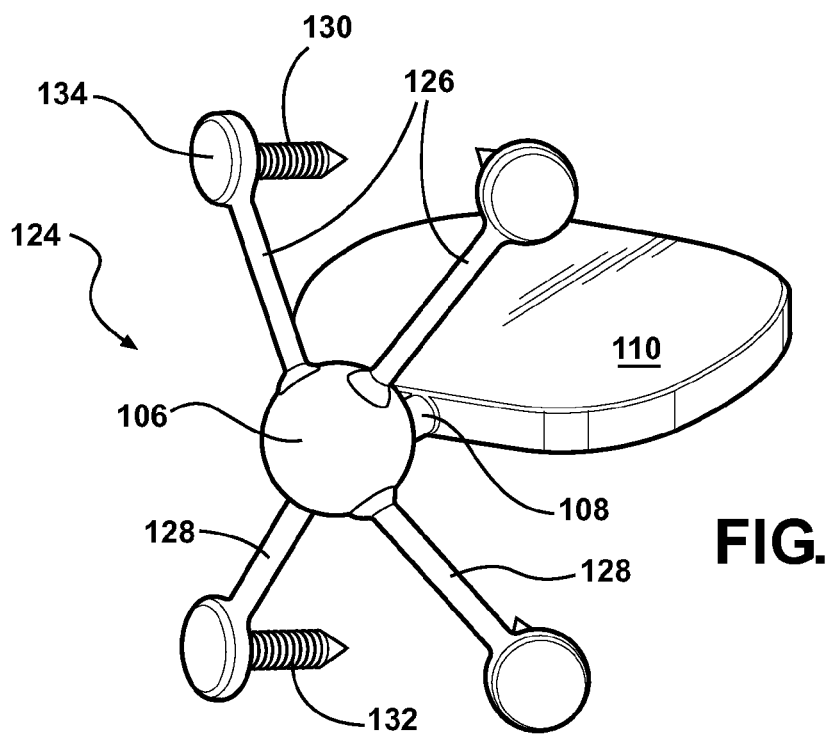
FIG. 13 is a perspective view similar to FIG. 11 of a related variant of retaining harness and depicting integrally formed engagement screws extending from remote extending ends of the upper and lower pairs of the pivotally eccentrically supported and elongated extending members.
Figure 14:
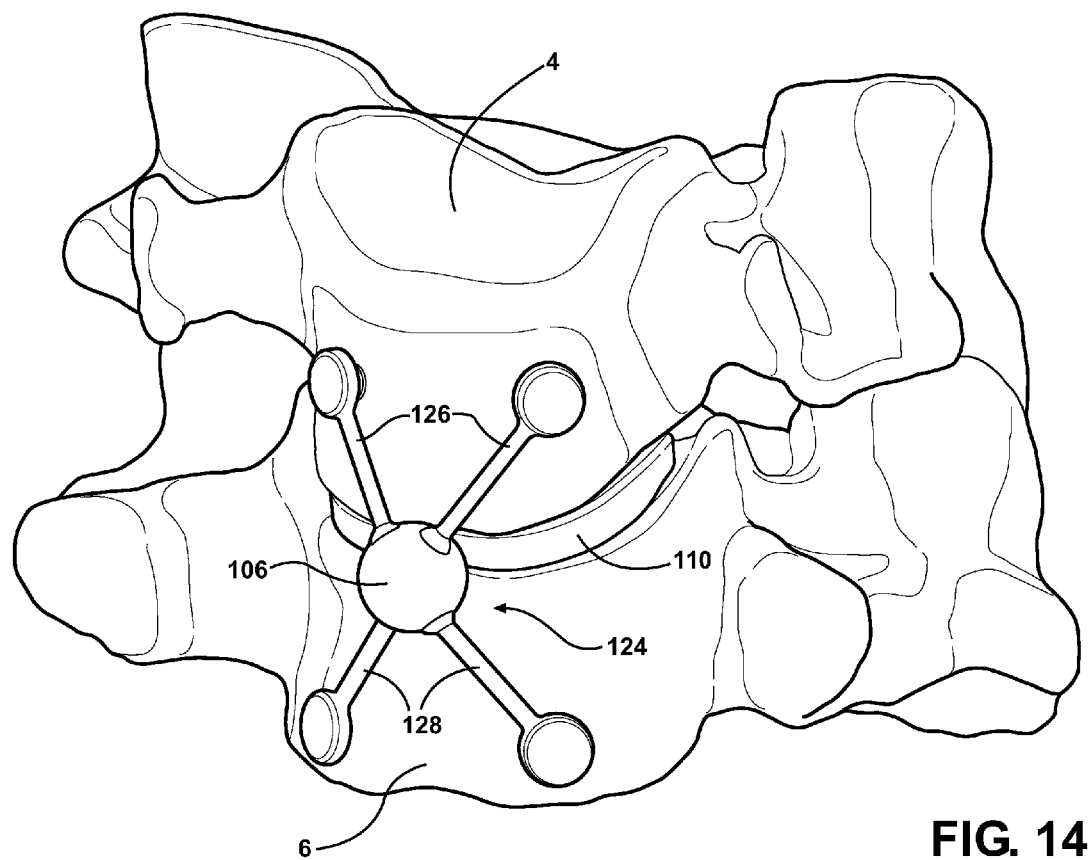
FIG. 14 is an environmental depiction of the retaining harness of FIG. 13 installed between succeeding vertebrae.

FIG. 13 is a perspective view similar to FIG. 11 of a related variant 124 of retaining harness, differing from the example of FIG. 11 only in the configuration of upper 126 and lower 128 pairs of elongated members, each of which depict integral screws 130 and 132 respectively extending from flattened end supports 134 and 136. As with the previously described embodiment 100 of retaining harness, and referring to FIG. 14, the manner of implanting the harness 124 relative to a pair of vertebrae 4 and 6 is illustrated and by which the desired degree of eccentric (i.e. both rotational and limiting pivotal) motion of the upper and lower pairs of elongated members relative to the socket retaining interiors of the spherical support 106 is established such as which provides increased spinal flexibility while safeguarding against pinching of the associated spinal nerve column and individual vertebral branches. In this fashion, an ideal balance is struck between providing some degree of flexibility (as opposed to fixed or immovable anchoring of the vertebrae through conventional plates and screws), without the undue risk of the pain associated with nerve pinching.

Additional variants to those depicted in FIGS. 11-14 include reconfiguring the elongated members both in number as well as shape and material consistency and properties. The screw mounting ends can also be reconfigured to reflect undercut mounting relationships with the vertebral bone locations.

Other changes can include the inter vertebral support inserting disks 110 being reconfigured to accommodate differing insertion applications as well as in order to provide different dynamic operational specifications. The harnesses may further be redesigned in order to anchor, in likewise eccentric and limited inter-moveable fashion, any greater number of vertebrae beyond the two illustrated in the examples depicted herein.

Having described my invention, other and additional preferred embodiments will become apparent to those skilled in the art to which it pertains, and without deviating from the scope of the appended claims:

I claim:

1. An implant support device adapted for use with succeeding spinal vertebrae, said device comprising:
   a flattened disk having a specified shape and size and which is adapted to being inserted between opposing surfaces of the succeeding vertebrae;
   a first pair of legs extending from a three dimensional portion integrally formed along an edge of said disk, said first pair of legs each exhibiting multi-axial flexibility in order to conform in extending fashion over a contoured surface of a first of the succeeding vertebrae, said legs each terminating in a fastener adapted to engaging a location associated with the first vertebra;
   a second pair of legs extending from said three dimensional portion in directions opposite said first pair of legs, said second pair of legs each exhibiting multi-axial flexibility in order to conform in extending fashion over a contoured surface of a second of the succeeding vertebrae, said second legs each terminating in a fastener adapted to engaging a location associated with the second vertebrae;
   each of said first and second pairs of legs further having a spherical shaped end opposite said fastener end, said spherical shaped ends resistively fitting within a spherical shaped socket defined in communicating fashion with surface locations of said three dimensional portion,
   said spherical ends facilitating motion between the vertebrae concurrent with cushioning the inner opposing surfaces of the first and second vertebrae.

2. The device as described in claim 1, further comprising a finger projection for spacing said three dimensional portion from said edge of said disk.

3. The device as described in claim 1, said fasteners further comprising integrally defined eyelet locations adapted to receive bone screws inserted through an open interior of each end configured eyelet such that enlarged heads of the screws abut against sides of said eyelets upon being adapted to anchoring within the vertebral bone locations.

4. The device as described in claim 1, said fasteners further comprising integrally formed end supported and bone engaging screws for anchoring within vertebra bone locations.

5. The device as described in claim 1, said disk further comprising an inter-vertebra cushion.

6. The device as described in claim 5, further comprising said cushion being constructed of a flexible and fluid injectable plastic and, upon being pre-positioned between succeeding vertebra, being injected with an internally ballasting and curable/settable composition for establishing a degree of supported and incremental movement between the vertebrae.

7. The device as described in claim 1, said three dimensional portion further comprising a spherical shape within which said spherical shaped individual pockets are formed.

* * * * *